United States Patent [19]

Phillips et al.

[11] Patent Number: 4,717,383
[45] Date of Patent: Jan. 5, 1988

[54] INJECTOR

[75] Inventors: Ian R. Phillips, Killara; Robert H. Lodge; Glen W. Bunyan, both of Dee Why, all of Australia

[73] Assignee: N.J. Phillips Pty. Limited, New South Wales, Australia

[21] Appl. No.: 760,393

[22] Filed: Jul. 30, 1985

[30] Foreign Application Priority Data

Jul. 31, 1984 [AU] Australia .................................. PG6305

[51] Int. Cl.⁴ .............................................. A61M 5/00
[52] U.S. Cl. .................................................. 604/135
[58] Field of Search ................................ 604/134–137, 604/192, 198, 263

[56] References Cited

U.S. PATENT DOCUMENTS 3,797,489  3/1974  Sarnoff ................................ 604/136
4,403,989  9/1983  Christensen et al. ............... 604/137
4,482,348 11/1984  Dent .................................. 604/263 X Primary Examiner—John D. Yasko
Attorney, Agent, or Firm—Lester Horwitz

[57] ABSTRACT

A rumen injector to inject a predetermined volume of medication into an animal, said injector having a body with a handle gripped by the user, a cylinder fixed to the body, a piston movably associated with the cylinder so as to define a variable volume space, a needle communicating with said space, and wherein said piston is movable to a cocked position where it is retained until automatically released upon said needle being inserted into the animal a predetermined distance.

13 Claims, 3 Drawing Figures

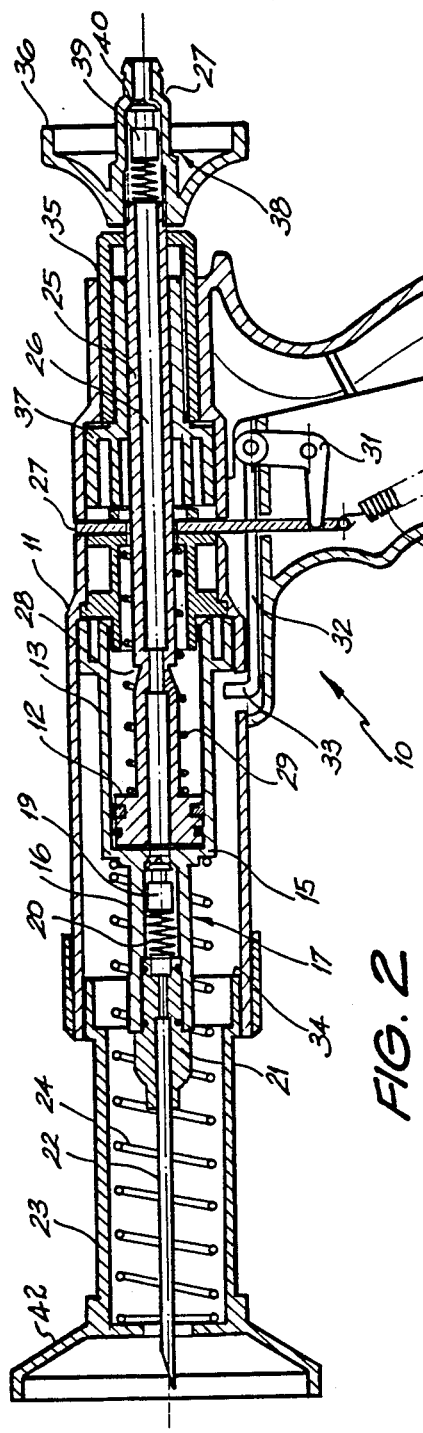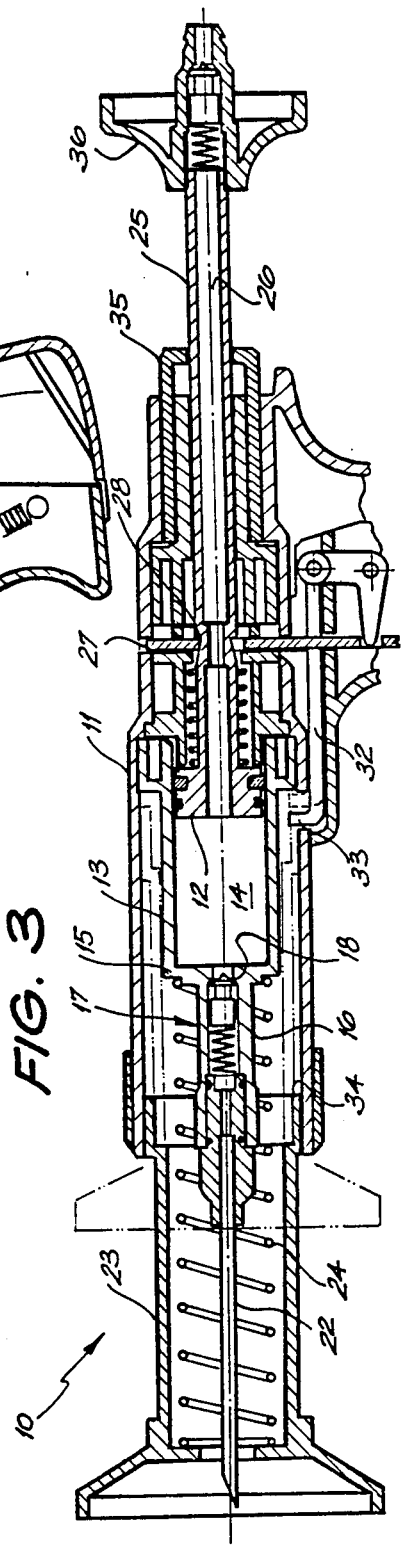

INJECTOR

The present invention relates to injector to deliver a required dose into an animal and more particularly but not exclusively to rumen injectors.

Known injector apparatus require the use of a trigger or similar arrangement to which the user must apply a force to operate the device in order to deliver a desired dose unit into an animal. Accordingly, these known devices require two actions, firstly the apparatus must be maintained at a desired location relative to the animal, and secondly the user must operate the device in order to deliver the dose to the animal.

The coordination of these two actions is often difficult with the result that the dose may be incorrectly delivered.

It is the object of the present invention to overcome or substantially ameliorate the above disadvantages.

There is disclosed herein an injector to deliver a predetermined dose into an animal, said injector comprising a hollow body, an interacting piston and cylinder mounted within the body and cooperating to define a variable volume working space, said piston or cylinder being fixed to said body and the other being movable longitudinally with respect to the axes of said cylinder between a rest position defining a minimum volume of said space and a cocked position defining a maximum volume for said space, delivery means including a needle fixed to said body and communicating with said space and through which said dose is delivered into said animal, an inlet means to be connected to a supply of liquid and communicating with said space so that liquid forming said dose may be delivered into said space, spring means biasing said piston or cylinder to said rest position, retaining means to selectively retain said piston or cylinder in said cocked position and operable to release said piston or cylinder, and release means to automatically operate said retaining means upon said needle being located a predetermined distance within said animal to thereby release said piston or cylinder.

A preferred form of the present invention will now be described by way of example with reference to the accompanying drawings wherein:

FIG. 2 is a schematic sectioned side elevation of the injector of FIG. 1; and

FIG. 3 is a schematic sectioned side elevation of the injector of FIG. 1, in a cocked position.

Figure 1:
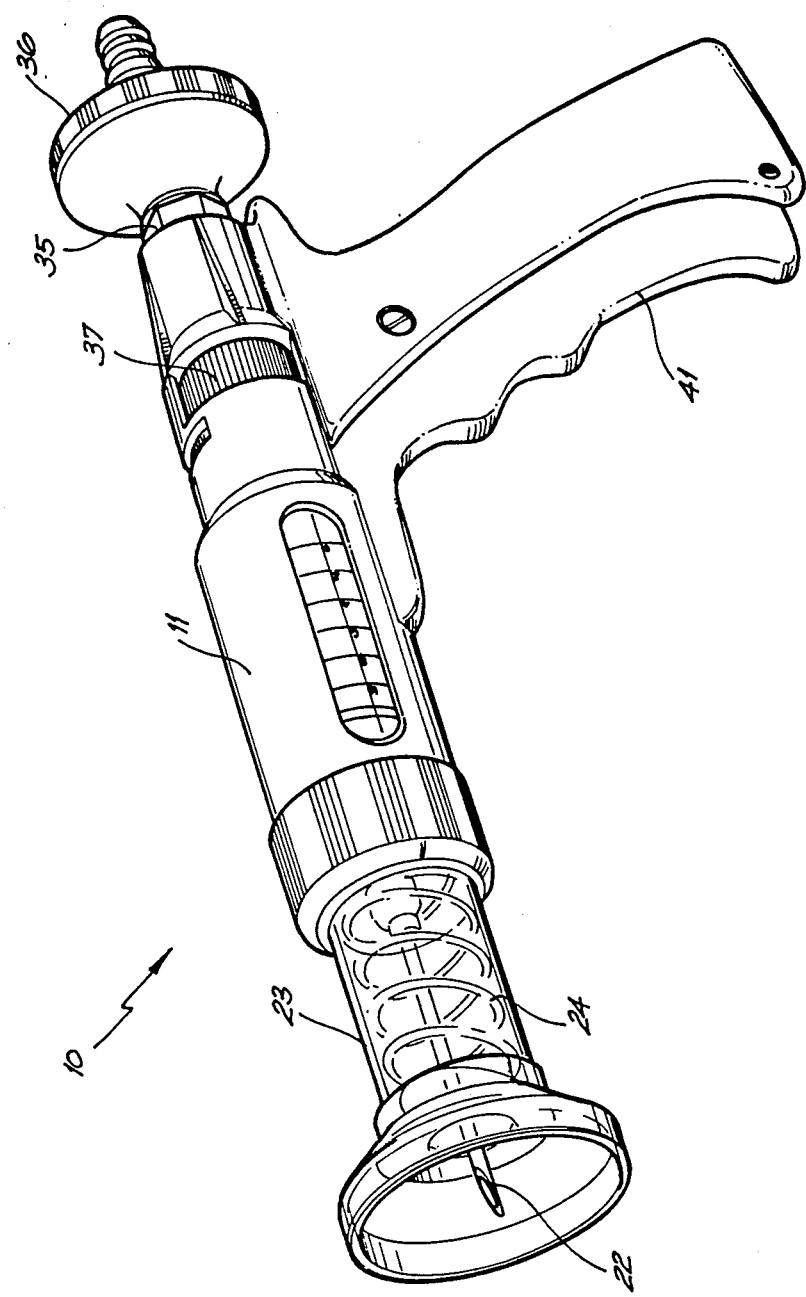
FIG. 1 is a schematic perspective view of a rumen injector.

In FIGS. 1 to 3 there is schematically depicted a rumen injector 10 to be used in injecting a desired dose into an animal. The injector 10 has a hollow body 11 within which there is mounted an interacting piston 12 and cylinder 13. The body 11 has a handle 41 which is gripped by the user. The cylinder 13 is fixed to the body 11 and the piston 12 longitudinally movable of the cylinder 13 so as to vary the volume of the working space 14. The cylinder 13 is closed at one end by a wall 15 from which there extends a tubular portion 16. Mounted within the tubular portion 16 is a one way valve assembly 17 including a seat 18 and a movable valve member 19 biased into engagement with the seat 18 by a spring 20. Fixed to the portion 16 by means of a needle mounting 21 is a needle 22 through which the dose is delivered into the animal. Surrounding the needle 22 is a retractable shroud 23 movable from the position depicted in FIGS. 2 and 3 to a retracted position telescopically located within the body 11 as depicted in ghost lines in FIG. 3. The shroud 23 is biased to a position covering the needle 22 by means of a spring 24. It should be appreciated that the one way valve assembly 17 restricts movement of liquid from the space 14 through the needle 22 to be delivered to the animal. It should also be noted that the shroud 23 has a flared end 42.

Extending from the piston 12 is a piston rod 25 defining a passage 26 which communicates with the space 14. The free end of the piston rod 25 is provided with an adaptor 27 which enables the injector 10 to be attached to a supply of liquid to be delivered to the space 14.

The piston 12 is movable from a rest position abutting the wall 15, to the cocked position depicted in FIG. 2, and is retained in the cocked position by means of a retaining member 27 engaging an abutment in the form of a lip 28 formed in the piston rod 25. The retaining member 27 is movable from a position engaging the lip 18 to a position releasing the piston rod 25. The piston 12 is then movable towards the wall 15. Engaging the piston 12 so as to bias the piston 12 in a direction towards the wall 15 is a spring 29. While biasing the retaining member 27 into engagement with the lip 28 is a spring 30. Also engaging the retaining member 27 is an L-shaped lever 31 pivotally mounted on the body 11 and engaging an actuating rod 32. The rod 32 has its extremity provided with a projection 33 positioned to engage the inner peripheral edge of the shroud 34. The rod 32, upon being moved longitudinally by the shroud 34, causes pivoting of the lever 31 and movement of the retaining member 27 from engagement with the lip 28.

Surrounding the piston rod 26 is a dose adjustment sleeve 35 which abuts a flange 36 to limit travel of the piston 12 to thereby adjust the volume of the dose delivered by the injector 10. The adjustment sleeve 35 is in threaded engagement with an adjustment member 37 which is manipulated by the user. Upon rotation of the adjustment member 37 longitudinal movement of the adjustment sleeve 35 results to thereby adjust the dose delivered by the injector 10. The flange 36 is also provided for the user of the gun to enable the user to cause movement of the piston rod 25 to move the piston 12 to the cocked position wherein the retaining member 27 is engaging the lip 28.

Located in the passage 26 is a one way valve assembly 38 which includes a movable valve member 39 which engages a valve seat 40. The valve assembly 38 cooperates with the valve assembly 39 to restrict the liquid to move through the injector 10 from the piston rod 25 to the needle 22.

In operation of the abovedescribed injector 10 the user of the injector 10 adjusts the volume of the dose delivered by rotation of the adjustment member 37. Thereafter, the user grips the flange 36 and causes movement of the piston towards the rear of the injector 10 until the retaining member 27 engages the lip 28. Thereafter, the user abuts the shroud 23 against the skin of the animal. Upon applying pressure to the handle 41, and forcing the injector 10 towards the animal, the shroud 23 is caused to telescopically move into the body 11. At the same time the needle 22 penetrates the animal and the shroud 2 will continue to move into the body 11 until the rod 32 is engaged and the lever 31 caused to pivot. Pivoting of the leer 31 causes the retaining member 27 to release the lip 28. Upon the lip 28 being released, the piston 12 moves within the cylinder 13 to reduce the volume of the space 14 thereby delivering a dose through the needle 22.

It should be appreciated that in the above described preferred embodiment, the cylinder 13 is fixed to the body 11 and the piston 12 is movable. However, the position of the piston 12 and cylinder 13 could be reversed with the piston 12 fixed to the body 11 and the cylinder 13 movable.

What we claim is:

1. An injector to deliver a predetermined dose into an animal, said injector comprising a hollow body, an interacting piston and cylinder mounted within the body and cooperating to define a variable volume working space, said piston or cylinder being fixed to said body and the other being movable longitudinally along the longitudinal axis of said piston and cylinder between a rest position defining a minimum volume of said space and a cocked position defining a maximum volume for said space, delivery means including a needle fixed to said body and communicating with said space and through which said dose is delivered into said animal, an inlet means to be connected to a supply of liquid and communicating with said space so that liquid forming said dose may be delivered into said space, spring means biasing said piston or cylinder to said rest position, retaining means to selectively retain said piston or cylinder in said cocked position and operable to release said piston or cylinder, and release means to automatically operate said retaining means upon said needle being located at predetermined distance within said animal to thereby release said piston or cylinder.

2. The injector of claim 1, wherein said release means is a release member adapted to abut said animal adjacent said needle, which release member is movable mounted on said body so as to be movable from an extended position to a retracted position, with said release member being adapted to engage said retaining means to cause release thereof upon reaching said retracted position.

3. The injector of claim 2, wherein said release member is a shroud generally surrounding said needle.

4. The injector of claim 2, further including a rod extending from the piston or cylinder, which ever is fixed to said body, which rod is movably supported by said body, a passage extending through said rod and forming part of said inlet means.

5. The injector of claim 4, wherein said retaining means includes an abutment formed on said rod, a retaining member movably supported by said body and movable from a first position engaging said abutment to retain said piston or cylinder in said cocked position, and a second position allowing movement of said abutment.

6. The injector of claim 5, wherein said retaining means further includes linkage means engaged by said release member, which linkage means causes movement of said retaining member from the first position thereof, to the second position thereof upon said release member being moved to a predetermined position relative to said body.

7. The injector of claim 6, wherein said linkage means includes an L-shaped lever pivotally mounted intermediate its ends, an actuating rod supported by said body and operatively engageable with one end of said lever, the other end of said lever being operatively associated with said retaining member to cause movement thereof, and wherein said actuating rod is engaged by said release member upon reaching said predetermined position so as to cause movement thereof to move said retaining member from the first position thereof, to the second position thereof.

8. The injector of claim 7, wherein said cylinder is fixed to said body and said piston is movable relative to said cylinder.

9. The injector of claim 8, wherein said release member is telescopically movable within said body to said predetermined position and is biassed by a spring to its extended position, and said piston is biased by a spring to a position minimising the volume of said space.

10. The injector of claim 9, further including adjustment means to limit the travel of said piston to thereby adjust the volume delivered by the injector.

11. The injector of claim 1 wherein the needle is permanently fixed within the body during entire operation of the injector.

12. The injector according to claim 3 wherein during operation of the injector upon applying pressure to the body and forcing the injector towards the animal the shroud caused to move telescopically into the body allowing the needle permanently fixed within the body to penetrate the animal.

13. The injector according to claim 12, wherein the pressure is applied to the body by an operator.

* * * * *